United States Patent [19]

Larson et al.

[11] Patent Number: 5,796,117
[45] Date of Patent: Aug. 18, 1998

[54] PREPARATION OF WATERBORNE SILANE/TITANIUM CHELATES COMPOSITION

[75] Inventors: Gerald L. Larson, Newtown, Pa.; James R. Steinmetz, Princeton, N.J.; Joel M. Zazyczny, Collegeville, Pa.

[73] Assignee: Huls America Inc., Somerset, N.J.

[21] Appl. No.: 679,852

[22] Filed: Jul. 15, 1996

[51] Int. Cl.$^6$ .................................................. C09K 3/00
[52] U.S. Cl. ............................................... 252/182.14
[58] Field of Search .................................. 252/182.14

[56] References Cited

U.S. PATENT DOCUMENTS

| | | | |
|---|---|---|---|
| 4,490,526 | 12/1984 | Amort et al. | |
| 5,073,195 | 12/1991 | Cuthbert et al. | 106/2 |
| 5,349,073 | 9/1994 | Horn et al. | |
| 5,428,103 | 6/1995 | Friebe et al. | |
| 5,565,291 | 10/1996 | Mayama et al. | 430/106.6 |

FOREIGN PATENT DOCUMENTS 1136548  12/1968  United Kingdom.

OTHER PUBLICATIONS

*Plastics Compounding* (reprint) Sep. 1987 Improved organosilane Systems for Highly Filled Acrylics.
Hüls AG Brochure Metal–acid ester/–chelates pre–1995.

*Primary Examiner*—Edward A. Miller
*Attorney, Agent, or Firm*—Abelman, Frayne & Schwab

[57] ABSTRACT

A stable aqueous solution of a silane/titanium chelate is prepared by (a) forming a mixture in alcoholic solution of bis-hydroxyethylaminopropyltriethoxysilane and a titanium chelate selected from the group consisting of titanium acetylacetonate, triethanolamine titanate and butyltitanate monomer;

(b) adding water to the mixture of step (a) in a quantity sufficient to effect the hydrolysis of the silane;

(c) completing the silane hydrolysis reaction; and (d) removing the alcohol from the solution.

The end product can be diluted further with water to provide a commercial formulation that is substantially free of VOC and has a shelf like of at least six months. The aqueous solution of the silane/titanium chelate can also include an organofunctional silane.

19 Claims, No Drawings

PREPARATION OF WATERBORNE SILANE/TITANIUM CHELATES COMPOSITION

FIELD OF THE INVENTION

The invention relates to chelated aqueous solutions of silane/titanium compounds having little or no volatile organic chemical (VOC) content, and from which essentially no alcohol or other solvent is released during use or application.

BACKGROUND OF THE INVENTION

Silane/titanate compounds have been used in a wide variety of polymer compounding applications. One important industrial use is as a sizing agent for glass fibers. Glass fibers that are to be used for reinforcing plastics are treated with a sizing agent to improve their adhesion, to reduce the sensitivity of the composition to moisture and to provide mechanical protection to the glass fiber. The sizing composition comprises an aqueous solution (usually 1% to 2%), of a film-forming composition, such as glycidylmethacrylate/vinyl acetate copolymer, a silane, wetting and antistatic agents, and a titanium compound, such as titanium acetylacetonate.

Other uses of silane/titanate compounds include the fixation of alkylsilanes to cellulosic materials, for example, as disclosed in U.S. Pat. No. 4,490,526 to Amort et al.; and the use of combinations of methacryloxysilanes with titanium chelates to prevent the "turnaround" or wicking of sizings to the surface of spools of silane-treated glass fibers.

Another important industrial use for silane/titanate additive systems is in highly-filled polymers, such as acrylics. In this application, the activity of organosilanes is increased as a result of the combination with titanium esters and zirconium esters, and produces significant reductions in the viscosity of highly-filled systems, as well as an improvement in certain of the physical properties of the cured polymer products. As reported by H. Hanisch et al., *Plastics Compounding*, Sep/Oct 1987, the combination is effective with a variety of fillers, including silicas, silicates, aluminas and carbonates.

In addition to the above examples, the chemical literature contains many other reports of the use of silane/titanate mixtures; however, all of these systems release organic vapors, or VOC, when used or applied. Environmental concerns have resulted in regulations requiring industry to greatly reduce, if not eliminate, the release of organic vapors. In many industrial fields such as the coatings industry, water-borne systems are being evaluated and adopted as replacements for solvent-borne systems. While this approach accomplishes the goal of reducing emissions of organic compounds into the atmosphere, the properties of the new water-borne systems are, in some instances, inferior to their solvent-borne counterparts.

It is therefore an object of the invention to provide a method for preparing silane/titanium mixtures that are aqueous solutions that contain no, or very low amounts of volatile organic compounds, such as the alcohols found in the compositions of the prior art.

It is another object of the invention to provide a method for preparing silane/titanium mixtures that are aqueous solutions that produce little or no VOC when used or applied.

It is a further object of the invention to provide waterborne mixtures of silane/titanium esters, or titanium chelates, that will produce equivalent or enhanced properties in the cured polymers as compared to their solvent-borne counterparts.

BRIEF DESCRIPTION OF THE INVENTION

The invention is directed to a method of preparing an aqueous solution of one or more silanes and a titanium chelate that is stable, i.e., that has a shelf life of at least six months. The novel mixture contains essentially no alcohol or like volatile organic compounds, thereby eliminating the health, environmental and flammability safety concerns associated with the VOC-containing compounds of the prior art.

The invention also includes novel aqueous titanium chelate and silane compositions produced in accordance with the process and which exhibit unexpected initial stability and a long shelf life.

The invention is based upon the discovery that N,N-bis-(2-hydroxyethyl)-3-aminopropyltriethoxysilane (also referred to as "bis-hydroxyethylaminopropyltriethoxysilane") itself functions as a chelate for transition metals and serves to stabilize the titanate component in aqueous solution. In the practice of the process of the invention, the bis-hydroxyethylaminopropyltriethoxysilane is combined with the titanate, as by agitation, and water is added to the mixture in a quantity sufficient to effect the complete hydrolysis of the silane; after the hydrolysis reaction is complete, the alcohol formed is removed, along with any alcoholic solvents present, as by vacuum stripping, and, in a preferred embodiment, water is added to bring the weight back to approximate the total weight of the original ingredients and to adjust the molal concentration of the solution.

The bis-hydroxyethylaminopropyltriethoxysilane is preferably added as an alcoholic solution to the titanium compound. In a preferred embodiment of the practice of the process, the bis-hydroxyethylaminopropyltriethoxysilane is added as a 62% solution by weight, of N,N-bis(2-hydroxyethyl)-3-aminopropyltriethoxysilane in ethanol, which is available from Huls America Inc. of Piscataway, N.J. under the designation B2408. The bis-hydroxyethylaminopropyltriethoxysilane can also be used in its pure form or as a solution in other common organic solvents that can readily be removed from the final chelate solution, as by vacuum stripping.

The titanium source is selected from the group consisting of titanium acetylacetonate, triethanolamine titanate and butyltitanate monomer. These compounds are commercially available. Other alkyltitanate monomers containing a $C_1$-$C_6$ alkyl group can also be used.

Deionized water is preferably used in the hydrolysis reaction and to make up the original weight of the solution following removal of the alcohol, preferably under reduced pressure.

DETAILED DESCRIPTION OF THE INVENTION

The following examples illustrate the present invention in several of its preferred embodiments and will enable those skilled in the art to understand it more completely. It is to be understood, however, that the invention is not limited solely to the examples given below. These illustrative examples demonstrate that the bis-hydroxyethylaminopropyltriethoxysilane does, itself, function as a chelate for transition metals and stabilizes the titanate in solution.

EXAMPLE 1

To a 150 ml round bottomed flask equipped with a magnetic stirrer were added 75 grams (0.15 mol) of N,N- bis(2-hydroxyethyl)-3-aminopropyltriethoxysilane as a 62% solution in ethanol and 19 grams (0.039 mol) of titanium acetylacetonate (TIACA 75) as a 75% solution in isopropyl alcohol. Following agitation for approximately one hour, 90 grams of deionized water was added and the reaction mixture was stirred for approximately 30 minutes to ensure complete hydrolysis.

The flask was placed onto a rotary evaporator and agitation was continued until the oil bath reached a temperature of 60° C. The alcohol was vacuum stripped from the solution at 28 inches of Hg.

Deionized water was added to the flask to make up a total weight of 164 grams. The silane/titanium chelate mixture contained no detectable amount of alcohol. The mixture appears as an amber liquid with a flash point greater than 90° C.

The stable water-borne silane/titanium chelate can be used as an additive in printing inks for improved adhesion, and in aqueous paints for improved adhesion, corrosion and heat resistance.

EXAMPLE 2

Using the same apparatus and step-wise procedure set forth in Example 1, 50 grams (0.1 mol) of bis-hydroxyethylaminopropyltriethoxysilane and 23 grams (0.05 mol) of triethanolamine titanate (TEAT) are mixed prior to addition of 81 grams of deionized water to the mixture. Following complete hydrolysis of the reaction mix and vacuum stripping to remove the alcohol reaction product and solvents, deionized water is added to the flask to bring the total weight of the solution to 135 grams. The appearance and properties of the chelate composition are similar to those of the product of Example 1.

EXAMPLE 3

Using the same apparatus and following the same step-wise procedure set forth in Example 1, 75 grams of bis-hydroxyethylaminopropyltriethoxysilane (0.15 mol) and 8.5 grams (0.025 mol) of butyltitanate monomer (BTM) are mixed prior to addition of 82.4 grams of deionized water to the mixture. Following completion of the hydrolysis reaction, the alcohol is recovered by vacuum stripping. The reaction mixture is brought to a total weight of 137 grams by addition of deionized water.

Other alkyl titanates having utility in the practice of the process include n-propyl and isopropyl compounds.

In the following examples, the invention is further illustrated by silanes having various functional moieties that are also added to the reaction mixtures described in the above examples. These organofunctional silanes are incorporated in the chelate composition of the product solution. As will be understood by those familiar with the art, the method utilized and the products obtained can be considered general for organofunctional silane coupling agents.

EXAMPLE 4

In a reaction vessel, 74.8 (0.15 mol) of bis-hydroxethylaminopropyltriethoxysilane as a 62% solution in ethanol was combined with 25.2 grams (0.052 mol) of titaniumacetylacetonate (TIACA 75) as a 75% solution in isopropyl alcohol. Following agitation for a one hour reaction period, 5.6 grams (0.025 mol) of aminopropyltriethoxysilane was introduced. The resulting solution was agitated for one additional hour. Thereafter, 70.9 grams of deionized water was added and the clear solution stirred for an additional one hour.

Alcohol and water were then co-distilled from the mixture under reduced pressure (final conditions: 28" vacuum, 60° oil bath.) After distillation, deionized water was added to bring the total weight of the solution to 141.8 grams.

EXAMPLE 5

In a reaction vessel, 74.8 grams (0.15 mol) of bis-hydroxyethylaminopropyltriethoxysilane as a 62% solution in ethanol was combined with 25.2 grams (0.052 mol) of titaniumacetylacetonate (TIACA 75) as a 75% solution in isopropyl alcohol. After agitation for a one hour reaction period, 4.46 grams (0.025 mol) of methyltriethoxysilane was introduced and stirring was continued for an additional one hour.

Thereafter, 70.1 grams of deionized water was introduced and, after a one hour agitation period, alcohol and water were distilled from the mixture under reduced pressure (final conditions: 28" vacuum, 60° C. oil bath.) The mixture was then diluted with deionized water to a final weight of 140.2 g.

EXAMPLE 6

In a vessel, 74.8 g (0.15 mol) of bis-hydroxyethylaminopropyltriethoxysilane as a 62% solution in ethanol was combined with 25.2 grams (0.052 mol) of titaniumacetylacetonate (TIACA 75) a 75% solution in isopropyl alcohol. Following a one hour reaction period, 1.55 grams (0.006 mol) of methacryloxypropyltrimethoxysilane (MEMO) was introduced and stirring continued for an additional one hour. Thereafter, 67.2 grams of deionized water was introduced and, after a one hour agitation period, alcohol and water were distilled from the reaction mixture under reduced pressure (final conditions: 28" vacuum, 60° C. oil bath.) The mixture was then diluted with water to a final weight of 134.3 g.

In addition to the specific organofunctional silanes identified in the Examples 4–6 above, the following coupling agents can be utilized in the practice of the process:

chloropropyltrimethoxysilane,

N-2-aminoethyl-3-aminopropyltrimethoxysilane, 3-glycidoxypropyltrimethoxysilane, 3-mercaptopropyltrimethoxysilane, vinyltriethoxysilane and vinyltrimethoxysilane.

The waterborne silane/titanium chelate compositions produced according to the process exhibit stability for a shelf-life that is at least six months.

I claim:

1. A method for preparing a stable aqueous solution of a silane/titanium chelate comprising the steps of
   (a) forming a mixture in alcoholic solution of N,N-bis-2-hydroxyethy)aminopropyltriethoxysilane and a titanium chelate selected from the group consisting of titanium acetylacetonate, triethanolamine titanate and butyltitanate monomer;
   (b) adding water to the mixture of step (a) in a quantity sufficient to effect the hydrolysis of the silane;
   (c) completing the silane hydrolysis reaction; and
   (d) removing the alcohol from the solution.

2. The method of claim 1 which comprises the further step of adding water to the solution after the alcohol has been removed.

3. The method of claim 1 where bis-hydroxyethylaminopropyltriethoxysilane is N,N-bis(2-hydroxyethyl)-3-aminoisopropyltriethoxysilane.

4. The method of claim 1 where the N,N-bis-hydroxyethylaminopropyltriethoxysilane and the titanium chelate are originally in the form of alcoholic solutions.

5. The method of claim 1, where deionized water is added in step (b).

6. The method of claim 1 which comprises the further steps of adding a second organofunctional silane compound to the mixture of step (a) and mixing said second organofunctional silane with the mixture of step (a).

7. The method of claim 6 where the second organofunctional silane compound is selected from the group consisting of amino propyltriethoxysilane, methyltriethoxysilane and methacryloxypropyltrimethoxysilane.

8. The method of claim 1 where the removal of alcohol in step (d) is effected by vacuum stripping.

9. The method of claim 8 where the solution is heated to about 60° C. during the vacuum stripping.

10. A process for preparing a stable aqueous solution of a silane/titanium chelate that is substantially free of VOC comprising the steps of:

(a) mixing alcoholic solutions of bis-hydroxyethylaminopropyltriethoxysilane and a titanium chelate selected from the group consisting of titanium acetylacetonate, triethanolomine titanate and butyltitanate monomer;

(b) reacting the mixture of step (a) with a sufficient quantity of water to effect the complete the hydrolysis of the silane compound; and (c) removing alcohol formed by the hydrolysis reaction of step (b) from the solution containing the product.

11. The process of claim 10 which further comprises:

(d) adding a predetermined amount of water to the solution containing the chelate prior to use.

12. A process for preparing a stable aqueous solution of a composition formed from a titanium chelate and at least two silane compounds, which aqueous solution is substantially free of VOC, the process comprising the steps of:

(a) forming a mixture in alcoholic solution of bis-hydroxyethylaminopropyltriethoxysilane and a titanium chelate selected from the group consisting of titanium acetylacetonate, triethanolomine titanate and butyltitanate monomer;

(b) mixing at least one organofunctional silane compound with the mixture of step (a);

(c) reacting the mixture of step (b) with water in a quantity that is sufficient to effect the complete hydrolysis of the silane compounds and form the chelate product; and (d) removing alcohol formed by the hydrolysis reaction of step (c) from the solution containing the chelate product.

13. The process of claim 12 which further comprises:

(e) adding a predetermined amount of water to the solution containing the chelate prior to use.

14. The process of claim 12 where the at least one organofunctional silane compound is selected from the group consisting of aminopropyltriethoxysilane, methyltriethoxysilane and methacryloxypropyltrimethoxysilane.

15. The process of claim 12 where deionized water is employed in step (c).

16. The process of claim 12 where the removal of the alcohol from the solution in step (d) is effected by vacuum distillation.

17. The method of claim 16 in which the distillation temperature does not exceed about 60° C.

18. A stable aqueous solution of a chelate formed by the hydrolysis reaction product of bis-hydroxyethylaminopropyltriethoxysilane and a titanate selected from the group consisting of monomer that is substantially free of VOC.

19. A stable aqueous solution of a chelate formed by the hydrolysis reaction product of bis-hydroxyethylaminopropyltriethoxysilane and at least one organofunctional silane selected from the group consisting of aminopropyltriethoxysilane, methyltriethoxysilane and methacryloxypropyltrimethoxysilane and a titanate selected from the group consisting of titanium acetylacetonate, triethanolamine titanate and butyltitanate, said chelate solution being substantially free of volatile organic compounds.

* * * * *